Figure 1:
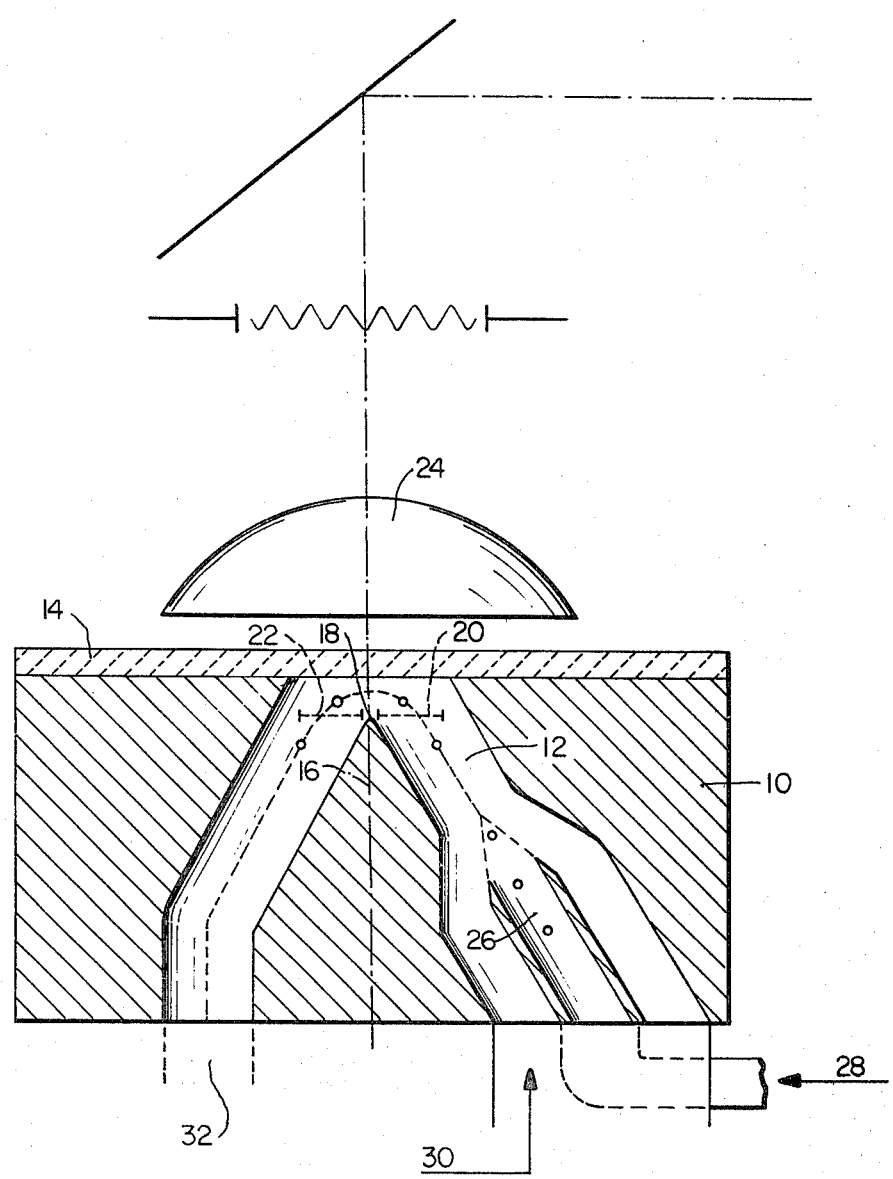

United States Patent [19]

Gohde

[11] 4,225,229

[45] Sep. 30, 1980

[54] APPARATUS FOR MEASURING CYTOLOGICAL PROPERTIES

[76] Inventor: Wolfgang Göhde, Stauffenbergstrasse 40, 4400 Münster, Fed. Rep. of Germany

[21] Appl. No.: 883,661

[22] Filed: Mar. 6, 1978

[30] Foreign Application Priority Data

Mar. 4, 1977 [DE] Fed. Rep. of Germany ....... 2709399

[51] Int. Cl.³ ........................ G01N 1/10; G01N 21/64; G01N 33/48
[52] U.S. Cl. .................................. 356/39; 250/461 B; 356/246
[58] Field of Search .................. 356/39, 246, 410–411, 356/440; 250/461, 461 B, 575–576; 422/93, 102

[56] References Cited

U.S. PATENT DOCUMENTS

| | | | |
|---|---|---|---|
| 3,740,665 | 6/1973 | Itzkan | 356/246 |
| 3,788,744 | 1/1974 | Friedman et al. | 356/39 |
| 3,811,777 | 5/1974 | Chance | 356/73 |
| 3,897,154 | 7/1975 | Hawes | 250/575 |
| 3,902,807 | 9/1975 | Fleming et al. | 356/410 |
| 3,916,205 | 10/1975 | Kleinerman | 250/461 |
| 3,984,307 | 10/1976 | Kamentsky et al. | 356/39 |

FOREIGN PATENT DOCUMENTS 7333009 3/1974 Fed. Rep. of Germany .

OTHER PUBLICATIONS

Stohr, M., "Double Beam Application in Flow Techniques & Recent Results", Pulse Cytophotometry, 1976, pp. 39–45.

*Primary Examiner*—Ronald J. Stern
*Assistant Examiner*—Wm. H. Punter
*Attorney, Agent, or Firm*—Roylance, Abrams, Berdo & Farley

[57] ABSTRACT

A flow chamber includes a flow passage having a knee with a window through which cells in liquid suspension pass. An optical system establishes an observation plane through the passage at the corner enclosed in the knee and illuminates the two portions separated by the corner with light at different wavelengths. Fluorescence of the cells is detected and measured.

13 Claims, 2 Drawing Figures

APPARATUS FOR MEASURING CYTOLOGICAL PROPERTIES

This invention relates to a system for detecting characteristics of cells suspended in a liquid medium and to a flow chamber for use in the system.

BACKGROUND OF THE INVENTION

Biological cells, such as cells taken from the human body, can be investigated by treating the cells with various chemical substances and observing and measuring luminous phenomena (e.g., fluorescence of the cells) occurring after this treatment and irradiation of the cells by light. By way of example, cells are stained with two different fluorescent dyes, one of which causes phenomena of fluorescence characteristic of the DNA and the other one characteristic of the protein of the cell.

To accomplish this, dyes are employed which show peaks, or maxima, of absorption at certain wavelengths during the fluorescence excitation. When using devices available prior to the present invention, errors occur in the case of simultaneous measurement, because the fluorescence spectra of the dyes utilized are comparatively broad and overlap one another. In these instruments part of the light of one dye invariably reaches the photomultiplier intended for the other dye. A device built for this purpose is described by M. Stohr in "Double Beam Application in Flow Technic and Recent Results", *Pulse-Cytophotometry*, 1976, pp. 39–45. The apparatus is equipped with an argon-ion laser and a helium-cadmium laser emitting at wavelengths of 448 nm. and 441 nm., respectively.

It also has special mirrors for 325 nm. According to Stohr, difficulties can be avoided if the points of interaction between a particle and the illuminating laser beams are physically separated. However, no solution is offered to the problem in that paper.

Other examples of prior art devices in this general field are U.S. Pat. Nos. 3,513,319; 3,541,336 and 3,609,048.

BRIEF DESCRIPTION OF THE INVENTION

It is a general object of the present invention to provide a device having two observation points or zones at which the flow and observation conditions are essentially identical. To attain this objective, the invention provides a device for measuring cells which are suspended in a liquid and which pass with the liquid through test points arranged in a flow channel of a flow chamber and are observable through windows in the channel wall, the cells being excited into fluorescence by two light sources producing different wavelengths, each one of which is assigned to an observation point. The device is characterized in that the observation points are arranged at the knee of the flow channel, with the inflow and outflow cross sections each forming one of the two observation points which are separated by the corner enclosed by the knee. Preferably, the outer wall of the knee opposite the enclosed corner is constructed as an observation window. According to the invention, this observation window and the passage areas of the test points extend substantially perpendicular to the bisectrix of the knee angle.

In one aspect of the invention, there is provided a flow chamber for use in an optical system for detecting characteristic of cells suspended in a liquid comprising a body having a transparent wall portion, and means in said body for defining a flow passage through which the liquid and cells can pass, said flow passage having first and second passage portions intersecting at said wall portion and forming an angle therebetween of less than 180°, said means including an edge between said first and second portions and spaced from said transparent wall portion and lying in a plane extending across said first and second portions, whereby cells in said liquid pass through said plane in one direction toward said wall portion and in the other direction away from said wall portion.

In another aspect, the invention comprises an apparatus for determining optical characteristics of cells comprising a flow chamber comprising a body having a substantially planar observation window therein, and means for defining a flow passage through said body, said passage having angularly related inlet and outlet portions intersecting at said window with the central axes of said portions extending through said window, said means including an edge parallel with said window and spaced therefrom, means for supplying cells in a liquid suspension to one end of said inlet passage portion, an optical system including lens means for establishing an observation plane through said passage portions, adjacent said edge and substantially parallel with said window, light source means for providing light at two different wavelengths and for illuminating, through said lens means, the cells passing through said observation plane so that the cells in the inlet portion of said plane are illuminated at one wavelength and the cells in the outlet portion are illuminated at the other wavelength, and means responsive to light emanating from said cells to provide an indication of a characteristic thereof.

In the device according to the invention, both observation points have substantially identical flow conditions. They are physically separated, yet are so close to one another that the two separate light sources required for illumination need not be expensive lasers. Instead, according to the invention, they may be two adjacent filters having different spectral or wavelength transmission characteristics and arranged between a primary light source and the observation point. By means of a conventional dichromatic beam splitter, the light from the primary light source is emitted by the two filters in accordance with the Kohler illumination principle to the two observation points, one of which receives the light of one filter and the other that of the other filter. Two photomultipliers are arranged behind the beam splitter, using a second beam splitter. Either of these photomultipliers receives the fluorescence from the particular observation point properly divided via half-side diaphragms. Accordingly, the whole assembly is of a substantially simpler design and is less expensive than the devices now in use. Nevertheless, with the apparatus built in accordance with the principles of the invention, it is possible to excite the cells separately and properly with respect to the exitation wavelengths of light during their passage through the two observation points, and to measure them separately and correctly with respect to the fluorescence wavelengths of light. Special adjusting hitherto intended to minimize any overlapping is no longer necessary. The cells may be fed to the observation points with envelope flow. Thus, simplification is achieved when compared with flow chambers operating with a cross flow. The two observation points are symmetrical to one another, either of them forming a section of the focusing plane of the objective that can be fixed properly. Further, it is possible to provide an objective with a large aperture. By virtue of the envelope flow arrangement and proper adjustment of the flow conditions, the cells can be passed through the two observation points practically one at a time.

Figure 2:
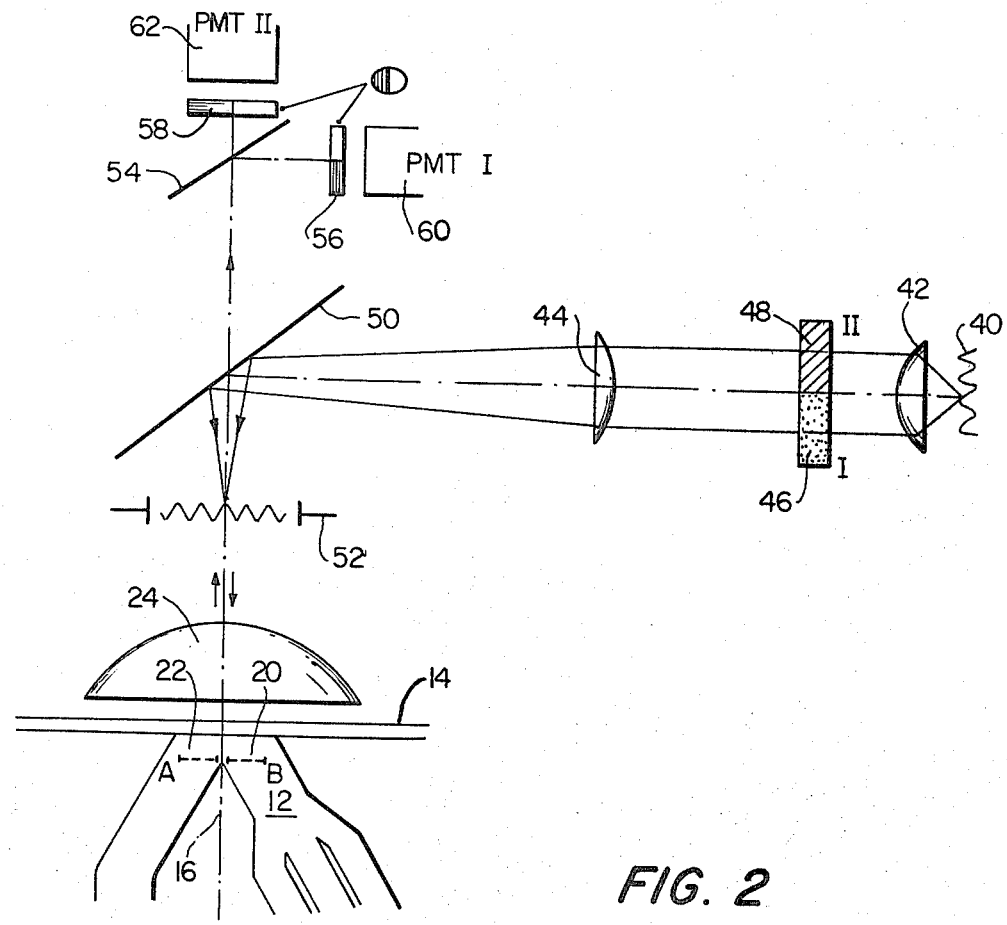

These and other advantages of the present invention will be readily apparent upon a consideration of the following description taken in conjunction with the accompanying drawings wherein:

FIG. 1 is a simplified side elevational view, schematic and in partial section, of a flow chamber according to the present invention; and FIG. 2 is a simplified schematic view of the overall apparatus in accordance with the present invention.

The device according to the invention shown in the drawings has a flow chamber 10 provided with a flow channel 12 which is bent like a knee about an inner separating corner member 16, the axes of the channels at the corner or edge forming an angle significantly less than 180°, normally between about 50° and about 90°, and preferably about 60°. The vertex of the knee angle is cut off and replaced by a transparent glass cover 14 extending substantially at right angles to the bisectrix of the corner 16.

Parallel with the surface of the plane glass cover 14 lies the cross section of the flow to be observed via an objective lens 24, the observation plane being marked by the dotted line A-B. This cross section lies partly in the inflow leg of channel 12 and partly in the outflow leg thereof, these passage portions being separated from each other by edge 18 of corner 16, Thus giving rise to the two observation zones or points 20 and 22, which are separated from one another and through which flow the particles or cells to be observed under substantially identical conditions. Edge 18 constitutes a line which is perpendicular to the plane of the paper and parallel with window plate 14.

The diameters of the flow passages in the zone of observation points 20 and 22 are determined by the nature of the particles under study. Depending on their size, the diameters vary between 0.1 and 0.5 mm. Diameters of 0.2 mm. are suitable for mammal cells.

Either or both of the observation zones may have slight differences in illumination level across the zone. To avoid measuring errors resulting therefrom, an envelope flow arrangement is employed with the object of passing all the cells through a predetermined point of the focusing plane, or observation point, so that all the cells are exposed to the same light energy. A cell suspension is fed to a feed channel 26 from a supply marked by arrow 28. This feed channel 26 ends in the inflow leg 12. An envelope of liquid is introduced to inflow leg 12 by a feeding mechanism comprising an annular inlet marked by arrow 30. The envelope liquid may consist of the same medium as the liquid in which are suspended the cells under study.

The outflow leg of channel 12 leads at 32 to a discharge tank. However, at 32 a sorting system for the cells may alternatively be connected to the outflow leg, the sorting being controlled by the readings taken at observation points 20 and 22.

The proper separation of observation points 20 and 22 by edge 18 of corner 16 permits a very simple design of the illumination system. A primary light source 40 is provided with a collector system 42 which makes parallel the rays of the beam of light emitted by source 40. Using lens 44, the light source is imaged into the "inner pupil" of the microscope objective. This corresponds to the Kohler illumination of the observation point. Two filters 46 and 48 are arranged side-by-side in the path of rays such that the beam of light of the primary light source 40 is divided into two different parallel beams arranged side-by-side. Depending on the filter characteristics, this gives rise to two different substantially monochromatic beams of light I and II, so that filters 46 and 48 may be considered secondary light sources. A dichromatic beam splitter 50 is arranged at a 45° angle to the optical axis of the objective 24. This optical axis of objective 24 corresponds to the bisectrix of corner 16 and is thus normal to the surface of observation points 20 and 22. Observation point 20 is illuminated through the use of the beam splitter by beam I which has traversed filter 46, and observation point 22 by beam II which has traversed filter plate 48.

With the aid of a second beam splitter 54, which is likewise arranged on the optical axis of objective 24 at a 45° angle behind beam splitter 50, the phenomena of fluorescence at observation points 20 and 22 are received by means of photomultipliers 60 and 62. There is arranged ahead of either multiplier a half-side closing diaphragm 56 in the eyepiece focal plane of the reflected light microscope such that the light reaches photomultiplier 60 from observation point 20 through diaphragm 56 while the latter is being shielded against light from observation point 22. Conversely, light from observation point 22 traverses beam splitter 54 and diaphragm 58 and reaches photomultiplier 62, while the latter is being shielded against light from observation point 20 by the half-side closing of diaphragm 58.

With the arrangement constructed in accordance with the teachings of the present invention, it is possible to work with a comparatively large inner pupil 52 and a correspondingly large aperture of objective 24.

While one certain advantageous embodiments has been chosen to illustrate the invention, it will be understood by those skilled in the art that various changes and modifications can be made therein without departing from the scope of the invention as defined in the appended claims.

What is claimed is:

1. A flow chamber for use in an optical system for detecting characteristics of cells suspended in a liquid, particularly for observation of the fluorescence characteristics of the cells upon excitation thereof by light sources having different wavelengths, comprising a body having a transparent wall portion; and means in said body for defining a flow passage through which the liquid and cells can pass, said flow passage having first and second passage portions intersecting at said wall portion and forming an angle therebetween of significantly less than 180°;

said means including an edge defining a knee between said first and second portions, said edge being spaced from said transparent wall portion and lying in a plane extending across said first and second passage portions, so that cells in liquid flowing through said passages pass through said plane in one direction toward said wall portion and through said plane in the other direction away from said wall portion on opposite sides of said edge whereby the fluorescence characteristics of the cells can be stimulated and observed through said wall portion as they pass in said respective directions through said plane.

2. A flow chamber according to claim 1 wherein said transparent wall portion is substantially planar and said edge is parallel to said wall portion.

3. A flow chamber according to claim 2 wherein said angle is an acute angle between about 50° and about 90°.

4. A flow chamber according to claim 3 wherein said acute angle is about 60°.

5. A flow chamber according to claim 1 wherein one of said first and second passage portions constitutes an inlet passage, said inlet passage having a central conduit for delivery of cells suspended in liquid and an annular conduit around said central conduit for delivery of liquid without cells, whereby envelope flow is established in said inlet passage to maintain said cells substantially centrally located in said flow passage.

6. An apparatus for determining optical characteristics of cells comprising
   a flow chamber comprising
      a body having a substantially planar observation window therein, and
      means for defining a flow passage through said body,
      said passage having angularly related inlet and outlet portions intersecting at said window with the central axes of said portions extending through said window,
   said means including an edge parallel with said window and spaced therefrom;
   means for supplying cells in a liquid suspension to one end of said inlet passage portion;
   an optical system including
      lens means for establishing an observation plane through said passage portions, adjacent said edge and substantially parallel with said window;
      light source means for providing light at two different wavelengths and for illuminating, through said lens means, the cells passing through said observation plane so that the cells in the inlet portion of said plane are illuminated at one wavelength and the cells in the outlet portion are illuminated at the other wavelength; and
   means responsive to light emanating from said cells to provide an indication of a characteristic thereof.

7. An apparatus according to claim 6 wherein said window forms a side of said passage at said intersection.

8. An apparatus according to claim 6 wherein said window and said observation plane are substantially perpendicular to a line bisecting the angle between said inlet and outlet portions.

9. An apparatus according to claim 6 wherein said inlet portion includes means for delivering said cell-liquid suspension to said observation plane in envelope flow.

10. An apparatus according to claim 6 wherein said light source means includes two filters arranged side-by-side and having different light wavelength transmission properties, and a primary light source illuminating said filters, said filters being disposed between said primary source and said observation plane.

11. An apparatus according to claim 6 wherein said means responsive to light emanating from said cells includes a photomultiplier arranged to receive light from cells in one side of said observation plane.

12. An apparatus according to claim 6 wherein said optical system includes beam splitters for coupling said light source means and said means responsive through said window from the same side.

13. A method of determining the spectral fluorescence response characteristics of dyed cells comprising the steps of
   optically defining a plane,
   passing a cell-containing liquid suspension sequentially through first and second zones of the plane in generally opposite directions, the zones being spatially separated;
   providing first and second separated beams of radiation at distinctly different wavelengths and focusing the beams at the zones in the plane, one of the zones being irradiated by one of the beams and the other zone by the other beam so that the cells in the suspension are sequentially irradiated at the two wavelengths; and
   separately detecting fluorescent emanations from the cells being irradiated in each of the zones.

* * * * *